United States Patent [19]

Carr et al.

[11] 3,985,888
[45] Oct. 12, 1976

[54] METHODS OF INDUCING SEDATION USING CERTAIN SPIROALKANONE-IMIDES

[75] Inventors: Albert A. Carr; Donald R. Meyer, both of Cincinnati, Ohio

[73] Assignee: Richardson-Merrell Inc., Wilton, Conn.

[22] Filed: Apr. 12, 1971

[21] Appl. No.: 133,372

Related U.S. Application Data

[62] Division of Ser. No. 844,613, July 24, 1969, Pat. No. 3,647,797.

[52] U.S. Cl. .................................. 424/267; 424/274
[51] Int. Cl.² ................ A61K 31/445; A61K 31/40
[58] Field of Search ............ 424/267, 274; 260/281

[56] References Cited
UNITED STATES PATENTS 3,379,731  4/1968  Walker ............................. 260/286

FOREIGN PATENTS OR APPLICATIONS 6,411,613  4/1965  Netherlands........................ 260/286

OTHER PUBLICATIONS

Koelsch: *J. Org. Chem.* 25: pp. 164–174 (1960).
Dews: Chemical Abstracts 47: 6043 i.
Campbell: J. Chem. Soc. vol. 1954 (pp. 1377–1380).

*Primary Examiner*—Leonard Schenkman
*Attorney, Agent, or Firm*—George W. Rauchfuss, Jr.; Eugene O. Retter

[57] ABSTRACT

Compounds having the general formula:

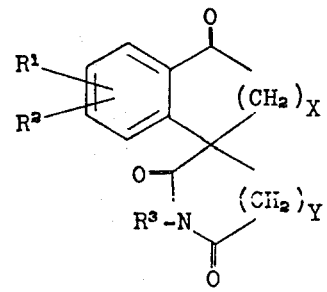

wherein $R^1$ and $R^2$ represent hydrogen, halogen, lower alkyl, lower alkoxy, or nitro, and wherein $R^1$ and $R^2$ may be the same or different. $R^3$ may be hydrogen or lower alkyl, and X and Y may be one or two. They have been found to be useful sedative type depressants of the central nervous system.

Most of the compounds having the general formula indicated above are new but others such as 2,3-dihydrospiro[naphthalene-1(4H),3'-piperidine]-2',4,6'-trione which has useful sedative properties have been reported in the literature.

6 Claims, No Drawings

METHODS OF INDUCING SEDATION USING CERTAIN SPIROALKANONE-IMIDES

RELATED APPLICATIONS

This application is a divisional application of application Ser. No. 844,613 filed July 24, 1969 and now U.S. Pat. No. 3,647,797.

BACKGROUND AND FIELD OF INVENTION

The synthesis of the spiroalkanone-imide, 2,3-dihydrospiro-[naphthalene-1(4H),3'-piperidine]-2',4,6'-trione, has been disclosed in the patent literature, i.e., Netherlands Pat. No. 6,411,613, and is said to be useful as an intermediate for the preparation of other compounds having diuretic, antihypertensive, and hypoglycemic properties. We have discovered that this compound and others of the present invention have central nervous system depressant properties and are useful as sedatives. The relatively non-toxic compounds of the present invention selectively inhibit spontaneous locomotor activity; that is, impaired motor coordination does not follow doses which reduce the motor activity. These substances also protect against the tonic extensor component of the maximal electroshock seizure and augment the central depressant effects of barbital and hexobarbital.

By way of illustration, 2,3-dihydrospiro-[naphthalene-1(4H),3'-piperidine]-2',4,6'-trione (Example 1), in mice, with an acute $LD_{50}$ orally or intraperitoneally of over 2000 mg/kg reduced spontaneous locomotor activity in the photocell chamber (Dews, P. B., Brit. J. Pharmacol., 8: 46 (1953)) to 50 percent of control activity following doses of about 150 mg/kg orally or 50 to 60 mg/kg intraperitoneally. There is no significant impairment of motor coordination as determined with the rotorod method (Kinnard, W. J. and Carr, C. J., J. Pharmacol. Exptl. Therap., 121: 354 (1957)), on the other hand, until doses of 900 mg/kg, p.o. or 500–900 mg/kg i.p. have been administered. The dose which protects half the mice against maximal electroshock (Woodbury, L. A. and Davenport, V. D., Arch. Int. Pharmacodyn, 92, 97 (1952)) is estimated to be 120 mg/kg, p.o. and 160–170 mg/kg i.p. Loss of the righting reflex produced by appropriate doses of barbital or hexobarbital is significantly prolonged by doses of about 300 mg/kg i.p. of the test substance.

The spiroalkanone-imide, 6-chloro-2,3-dihydro-1'-methylspiro-[naphthalene-1(4H),3'-piperidine]-2',4,6'-trione (Example 18) is particularly useful as a sedative and has substantially greater activity than the known compound mentioned above as shown in the following table.

The preparation of the compound of these examples. Example 1 describes a two-step sequence in which the first intermediate is not isolated but is used directly to give the desired product. Thus beginning with commercially available starting materials, the desired product is the first isolated product. Example 2 describes the same general synthetic procedure of Example 1 except that the intermediate is isolated and purified before use. Example 4 is essentially the method described by Koelsch, C. F., J. Org. Chem. 25, 164–74 (1960).

The 7,8-dimethoxy analog of the 6,7-dimethoxy compound of Example 11 has been described by Horning and Schock, Jr., J. Am. Chem. Soc., 70, 2945–49 (1948).

EXAMPLE 1

To a stirred mixture of 58.6 grams (0.5 M) of phenylacetonitrile and 150 grams (1.5 M) of ethyl acrylate was carefully added sodium methoxide in small increments (about 0.1 g). The exothermic reaction was controlled by ice bath cooling to keep the reaction mixture at 50° C. When further additions of sodium methoxide were no longer exothermic, the reaction mixture was stirred for one half hour more and the excess ethyl acrylate removed under reduced pressure on a steam bath. The resulting oil was added to 1.5 kg of polyphosphoric acid and stirred on a steam bath for 3 hours. After cooling to about 50° C., 0.5 liter of chloroform was added followed by additions of crushed ice until the aqueous phase was free-flowing. The chloroform layer was separated and combined with three 150 ml chloroform extracts of the aqueous layer. The organic phase was then dried over anhydrous magnesium sulfate, filtered and concentrated to a semi-solid residue. Recrystallization from acetone gave 2,3-dihydrospiro[naphthalene-1(4H),3'-piperidine]-2',4,6'-trione, melting point 197°–199° C.

EXAMPLE 2

A mixture of 350 grams of polyphosphoric acid and 21.6 grams (0.07 M) of diethyl γ-cyano-γ-phenylpimelate was stirred and heated on a steam bath for 3.5 hours. After cooling to 50°–60° C., 500 ml of chloroform was added followed by enough crushed ice to give a free-flowing aqueous layer. The separated chloroform layer was combined with three 100 ml chloroform extracts of the aqueous layer, dried over anhydrous magnesium sulfate, filtered and concentrated at reduced pressure to a solid residue. The resulting crystal mass was recrystallized from acetone and then isopropanol to give 12.7 grams (77%) of 2,3-dihydrospiro[naphthalene-1(4H),3'-piperidine]-2',4,6'-trione, melting point 197°–199° C.

| Compound | Activities: All Values mg/kg (Mice) | | |
|---|---|---|---|
| | Spontaneous Locomotor Activity: Depressant Dose 50% | Loss of Motor Coordination, $ED_{50}$ | Anticonvulsant Protective Dose 50% (Maximum Electroshock) |
| Example 1 | 150, oral<br>50–60, i.p. | 900, oral<br>500–900, i.p. | 120, oral<br>160–170, i.p. |
| Example 18 | 13, oral | 285, oral | |

PREPARATION OF SPIROALKANONE-IMIDES

The general procedures used in Examples 1, 2, and 3 which follow have not been previously described for The required diethyl γ-cyano-γ-phenylpimelate was prepared by reacting phenylacetonitrile with ethyl acrylate according to the general method of Koelsch, J. Am. Chem. Soc., 65, 437 (1943). This product, boiling point 148°–151° C. at 0.04 mm [Branchini et al., *Ann. Chim.* (Rome) 51, 1382 (1961) report 170°–172° C. at 0.2 mm] was obtained in addition to the mono-Michael addition product reported by Koelsch.

EXAMPLE 3

Five (5) grams (0.0179 M) of γ-carbamoyl-γ-phenylpimelic acid prepared by the method of Koelsch, *J. Org. Chem.*, 25, 164 (1960), in 100 ml of concentrated sulfuric acid were heated on a steam bath for two hours. The cooled reaction mixture was poured with stirring into crushed ice. The separated solid was washed with sodium bicarbonate solution. Recrystallization from 30 ml of acetone solution (treated with activated charcoal) gave 1.5 grams (34.5%) of 2,3-dihydrospiro-[naphthalene-1(4H),3'-piperidine]-2',4',6'-trione.

EXAMPLE 4

Two hundred (200) grams (0.76 M) of 3-phenyl-2,6-dioxopiperidine-3-propionic acid, prepared by the method of Koelsch, *J. Org. Chem.*, 25, 164 (1960), and 500 ml of concentrated sulfuric acid were heated on a steam bath with stirring for 1.5 hours. The mixture was cooled to room temperature and poured over crushed ice with stirring. The light tan colored precipitate which separated was water washed and filtered. This material was combined with a second crop which separated on standing and both were stirred in water and treated with five percent sodium carbonate solution until just alkaline. The precipitate was collected and water washed. The precipitate was recrystallized from acetone to give a total of 144.6 grams (82.4%) of 2,3-dihydrospiro-[naphthalene-1(4H), 3'-piperidine]-2',4',6'-trione, melting point 198°–200° C.

EXAMPLE 5

To 24.3 grams (0.1 M) of 2,3-dihydrospiro-[naphthalene-1(4H),3'-piperidine]-2',4,6'-trione in 100 milliliters of dry dimethylformamide was added with stirring 5.4 grams (0.1 M) of sodium methoxide. This was followed by 17.0 milliliters of dimethyl sulfate. The reaction mixture became clear and was slightly exothermic. After stirring for 15 minutes, 50 milliliters of solvent was removed at reduced pressure on a steam bath. The resulting solution was cooled and added to 1 liter of ice water. The resulting precipitate was collected and washed with 5 per cent sodium hydroxide solution and finally with water. Recrystallization from butanone-petroleum ether (70°–90°) and then from aqueous ethanol gave 18.4 grams (17.5%) of 1'-methyl-2,3-dihydrospiro-[naphthalene-1(4H),3'-piperidine]-2',4,6'-trione, melting point 136°–137.5° C.

EXAMPLE 6

To 24.3 grams (0.1 M) of 2,3-dihydrospiro-[naphthalene-1(4H),3'-piperidine]-2',4,6'-trione in 300 milliliters of dry dimethylformamide maintained under nitrogen atmosphere was added with stirring 4.37 grams (0.1 M) of a 55 per cent suspension of sodium hydride in mineral oil. After stirring for five minutes, 16.0 grams (0.1 M) of diethyl sulfate were added in one portion. The slightly exothermic reaction mixture was allowed to stir for a short time and concentrated hydrochloric acid was added dropwise until the reaction mixture was slightly acidic. The reaction solvent was removed under reduced pressure at steam bath temperature and the resulting oil extracted into ether. The ether extracts were washed with 5 percent sodium hydroxide solution, water, and then dried (MgSO$_4$). After filtration, the ether was removed, leaving a residue, which was recrystallized from diethyl ether to give 34.9 grams (64%) of 1'-ethyl-2,3-dihydrospiro-[naphthalene-1(4H),3'-piperidine]-2',4,6'-trione, melting point 85.5°–89° C.

This compound has sedative properties and is believed to be new.

EXAMPLE 7

A mixture of 93 grams (0.32 M) of 3-(p-methoxyphenyl)-2,6-dioxopiperidine-3-propionic acid and 930 grams of polyphosphoric acid were stirred at steam bath temperature for one hour. The partially cooled mixture was poured onto ice with stirring. The resulting precipitate was filtered and recrystallized from isopropyl alcohol-water to give 74 grams (84%) of 6-methoxy-2,3-dihydrospiro-[naphthalene-1(4H),3'-piperidine]-2',4,6'-trione, melting point 213.5°–215° C.

The required 3-(p-methoxyphenyl)-2,6-dioxopiperidine-3-propionic acid was obtained from 3-(p-methoxyphenyl)-1,3,5-pentanetricarbonitrile [*J. Chem. Soc.*, 1204 (1945)] according to the general method of Koelsch, *J. Org. Chem.*, 25, 164 (1960).

EXAMPLE 8

Following the procedure noted in Example 5, 84.0 grams (0.31 M) of 6-methoxy-2,3-dihydrospiro-[naphthalene-1(4H),3'-piperidine]-2',4,6'-trione was used to obtain 20.2 grams (23%) of 2,3-dihydro-6-methoxy-1'-methylspiro[naphthalene-1(4H),3'-piperidine]-2',4,6'-trione, melting point 116°–117.5° C.

This compound has sedative properties and is believed to be new.

EXAMPLE 9

Following the method of Example 7, 87.0 grams of 2,6-dioxo-3-(p-tolyl)-3-piperidinepropionic acid was cyclized to give 73.1 grams (92%) of 2,3-dihydro-6-methylspiro[naphthalene-1(4H),3'-piperidine]-2',4,6'-trione, melting point 252.5°–254° C. This material was purified from dilute acetic acid solution.

The required 2,6-dioxo-3-(p-tolyl)-3-piperidinepropionic acid was prepared by treating 3-(p-tolyl)-1,3,5-pentanetricarbonitrile [*J. Indian Chem. Soc.*, 29, 201 (1952)] with hydrochloric acid according to the method of Koelsch, *J. Org. Chem.*, 25, 164 (1960). This intermediate melted at 173.5°–175° C. after recrystallization from ethyl acetate.

This compound has sedative properties and is believed to be new.

EXAMPLE 10

Following the procedure noted in Example 5, 38.6 grams (0.15 M) of 2,3-dihydro-6-methylspiro-[naphthalene-1(4H),3'-piperidine]-2',4,6'-trione was methylated to give 32.5 grams (80%) of 1',6-dimethyl-2,3-dihydrospiro-[naphthalene-1(4H),3'-piperidine]-2',4,6'-trione, melting point 146°–147.5° C. from isopropyl alcohol.

This compound has sedative properties and is believed to be new.

EXAMPLE 11

Unpurified dimethyl γ-cyano-γ-(3,4-dimethoxyphenyl)pimelate, prepared from 334 grams of 3,4-dimethoxyphenylacetonitrile as described by Horning et al., *J. Am. Chem. Soc.*, 74, 773 (1942), was added with stirring to 3.0 kg of polyphosphoric acid. This reaction mixture was stirred at 110° C. for 2 hours and poured into 6.0 liters of crushed ice with stirring. The resulting solid was filtered and recrystallized from isopropyl alcohol-water to give 65.8 grams (18%) of 2,3-dihydro-6,7-dimethoxyspiro-[naphthalene-1(4H),3'-piperidine]-2',4,6'-trione, melting point 269°–271° C.

This compound has sedative properties and is believed to be new.

EXAMPLE 12

Following the procedure of Example 5, 30.3 grams (0.1 M) of 2,3-dihydro-6,7-dimethoxyspiro-[naphthalene-1(4H),3'-piperidine]-2',4,6'-trione was methylated to give 18.4 grams (58%) of 2,3-dihydro-6,7-dimethoxy-1'-methylspiro-[naphthalene-1(4H),3'-piperidine]-2',4,6'-trione. The product was purified from acetone-ethyl acetate solution, melting point 168°–170° C.

This compound has sedative properties and is believed to be new.

EXAMPLE 13

A mixture of 310 grams of polyphosphoric acid and 30.24 grams (0.1 M) of diethyl β-cyano-β-phenyladipate, prepared by the general method of Branchini et al., *Annali di Chimica*, 51, 1382 (1961), *Chem. Abstr.*, 56, 15362f (1962), were heated and stirred under nitrogen atmosphere on a steam bath for five hours. The reaction mixture was poured into an icewater slurry keeping the mixture temperature at about 10° C. by additions of crushed ice. Solid potassium carbonate was added to the reaction mixture until the pH was five. On cooling overnight, a precipitate formed. Careful crystallization from acetone and then from isopropyl alcohol gave 1.1 grams (4.4%) of spiro-[indane-1,3'-piperidine]-2,3,6'-trione, melting point 227°–228° C.

This compound has sedative properties and is believed to be new.

EXAMPLE 14

The combined filtrates from the purification of spiro-[indane-1,3'-piperidine]-2',3,6'-trione, described in Example 13, were concentrated and cooled to give a solid which was purified by elution from a 4.5 cm. × 28 cm. activated alumina column using the sequence of tetrahydrofuran, acetone, ethyl acetate, and ethanol as eluting solvents. The material obtained by removal of the ethanol melted at 202°–205° C. After several recrystallizations this material, 2,3-dihydrospiro[naphthalene-1(4H),3'-pyrrolidine]-2',4,5'-trione, 8.4 grams, melted at 204.5°–205.5° C.

This compound has sedative properties and is believed to be new.

EXAMPLE 15

A mixture of 156.5 grams (0.57 M) of 2,6-dioxo-3-(o-tolyl)piperidinepropionic acid and 900 ml of concentrated sulfuric acid were reacted according to the method of Example 4. There was obtained 128.5 grams (88%) of 2,3-dihydro-8-methylspiro-[naphthalene-1(4H),3'-piperidine]-2',4,6'-trione, melting point 285°–287° C. from acetic acid.

This compound has sedative properties and is believed to be new.

The required 2,6-dioxo-3-(o-tolyl)piperidinepropionic acid was prepared from 3-(o-tolyl)-1,3,5-pentanetricarbonitrile [J. Indian Chem. Soc., 29, 201 (1952)] and hydrochloric acid according to the method of Koelsch, *J. Org. Chem.*, 25, 164 (1960). This propionic acid derivative melted at 202-203.5° C. after recrystallization from methanol-water.

EXAMPLE 16

Methylation of 51.5 grams (0.2 M) of 2,3-dihydro-8-methylspiro-[naphthalene-1(4H),3'-piperidine]-2',4,6'-trione according to the method of Example 5, gave 39.5 grams (73%) of 2,3-dihydro-1',8-dimethylspiro-[naphthalene-1(4H),3'-piperidine]-2',4,6'-trione, melting point 117.5°–181° C. from isopropyl alcohol.

This compound has sedative properties and is believed to be new.

EXAMPLE 17

Following the method described in Example 4, 30.0 grams (0.1 M) of 3-(p-chlorophenyl)-2,6-dioxopiperidine-propionic acid and 620 grams of polyphosphoric acid were reacted to give 18 grams (64%) of 6-chloro-2,3-dihydrospiro[naphthalene-1(4H),3'-piperidine]-2',4,6'-trione, melting point 282.5°–284° C., from acetic acid.

This compound has sedative properties and is believed to be new.

The required 3-(p-chlorophenyl)-2,6-dioxopiperidinepropionic acid was obtained from 3-(p-chlorophenyl)-1,3,5-pentanetricarbonitrile [J. Am. Chem. Soc., 65, 23 (1943)] according to the method of Koelsch, J. Org. Chem., 25, 164 (1960). The propionic acid melted at 171.5°–173° C. after purification from aqueous acetic acid.

EXAMPLE 18

Methylation of 6-chloro-2,3-dihydrospiro-[naphthalene-1(4H),3'-piperidine]-2',4,6'-trione according to the method of Example 5 gave 6-chloro-2,3-dihydro-1'-methylspiro[naphthalene-1(4H),3'-piperidine]-2',4,6'-trione, melting point 164.5°–167° C.

This compound has sedative properties and is believed to be new.

EXAMPLE 19

A total of 14.1 grams (0.06 M) of 2,3-dihydrospiro-[naphthalene-1(4H),3'-piperidine]-2',4,6'-trione was added in small portions to 100 milliliters of nitric acid (d = 1.4) cooled to −5° to −10° C. This temperature was maintained for 15 minutes and then allowed to warm to 0° C. The reaction mixture was poured into an ice-water mixture and filtered. The precipitate was recrystallized from aqueous acetone and then from acetic acid and then from an acetone-isopropyl alcohol-ethyl acetate mixture. Recrystallization from dioxane followed by chromatographic purification from a silica gel column (eluted by dioxane) gave 2,3-dihydro-6-nitrospiro-[naphthalene-1(4H),3'-piperidine]-2',4,6'-trione, melting point 273°–275° C.

This compound has sedative properties and is believed to be new.

PREFERRED EMBODIMENTS

The compounds of the present invention may be administered orally, parenterally by injection, or in the form of suppositories. The compounds of the invention are administered to patients in amounts between 0.02 to 20 mg/kg of body weight. An effective oral dose for an adult will be between 10 milligrams to 1,000 milligrams per dose and may be conveniently administered orally in the form of 10 to 500 milligram tablets which can be prepared as follows:

Twenty-five (25) parts by weight of the desired spiroalkanone-imide is mixed with 16 parts by weight of powdered sugar containing 3 percent by weight of starch, 16 parts by weight of lactose, and 20 parts by weight of corn starch, and the mixture is put through a fine screen. The screened material is then granulated with water in conventional manner, put through a coarse screen, and separated on trays and dried. The granulation is passed through a 10 to 12 mesh screen and 0.8 parts by weight of magnesium stearate and 2.2 parts by weight of corn starch are mixed in. The powdered material is then compressed into tablets containing 10 to 500 milligrams per tablet of the spiroalkanone-imide.

Of course, the spiroalkanone-imides can be prepared in suspension form for oral administration and in the form of suppositories containing 5 to 25 milligrams of the drug for use by small children and 10 to 100 milligrams per suppository for use by adults.

We claim:

1. A method of inducing sedation which comprises administering to a patient a compound of the formula:

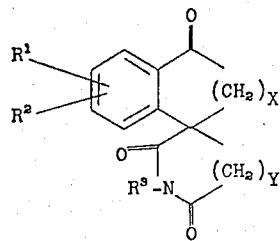

wherein $R^1$ and $R^2$ represent hydrogen, halogen, lower alkyl, lower alkoxy, or nitro, and wherein $R^1$ and $R^2$ may be the same or different; $R^3$ may be hydrogen or lower alkyl; and X and Y may be one or two, in amounts between 0.02 milligram to 20 milligrams per kilogram of body weight.

2. The method of claim 1 wherein the compound is 2,3-dihydrospiro-[naphthalene-1-(4H),3'-piperidine]-2',4',6'-trione.

3. The method of claim 1 wherein the compound is 6-chloro-2,3-dihydro-1'-methylspiro-[naphthalene-1(4H),3'-piperidine]-2',4',6'-trione.

4. The method of claim 1 wherein the compound is 1'-methyl-2,3-dihydrospiro-[naphthalene-1(4H),3'-piperidine]-2',4',6'-trione.

5. The method of claim 1 wherein the compound is 1'-ethyl-2,3-dihydrospiro-[naphthalene-1(4H),3'-piperidine]-2',4',6'-trione.

6. The method of claim 1 wherein the compound is 6-chloro-2,3-dihydrospiro[naphthalene-1(4H),3'-piperidine]-2',4',6'-trione.

* * * * *

UNITED STATES PATENT AND TRADEMARK OFFICE
CERTIFICATE OF CORRECTION

PATENT NO. : 3,985,888
DATED : October 12, 1976
INVENTOR(S) : Albert A. Carr and Donald R. Meyer It is certified that error appears in the above—identified patent and that said Letters Patent are hereby corrected as shown below:

```
Column 3, line 51, "(17.5%)" should read "(71.5%)".
Column 5, line 44, "2,3,6'-" should read "2',3,6'-".
Column 6, line 20, "117.5°-181°C." should read
"177.5°-181°C."
```

Signed and Sealed this

Third Day of January 1978

[SEAL]

Attest:

RUTH C. MASON
Attesting Officer

LUTRELLE F. PARKER
Acting Commissioner of Patents and Trademarks